United States Patent [19]

Li et al.

[11] Patent Number: 5,786,224
[45] Date of Patent: Jul. 28, 1998

[54] REAGENT AND METHOD FOR DIFFERENTIAL DETERMINATION OF LEUKOCYTES IN BLOOD

[75] Inventors: Yi Li; Carole Young, both of Miami, Fla.; Timothy J. Fischer, Raleigh, N.C.

[73] Assignee: Coulter Corporation, Miami, Fla.

[21] Appl. No.: 496,469

[22] Filed: Jun. 29, 1995

[51] Int. Cl.$^6$ .................................................. G01N 33/48
[52] U.S. Cl. .................................. 436/63; 436/8; 436/10; 436/17; 436/66; 436/164; 436/166; 436/172; 436/175; 436/176; 435/2
[58] Field of Search ......................................... 436/8, 10, 17, 436/18, 63, 66, 164, 166, 171, 172, 175, 176; 435/2

[56] References Cited

U.S. PATENT DOCUMENTS

| | | | |
|---|---|---|---|
| 4,286,963 | 9/1981 | Ledis et al. | 436/63 |
| 4,485,175 | 11/1984 | Ledis et al. | 436/63 |
| 4,853,338 | 8/1989 | Benezra et al. | 436/66 |
| 4,978,624 | 12/1990 | Cremins | 436/17 |
| 5,116,539 | 5/1992 | Hamaguchi et al. | 252/408.1 |
| 5,125,737 | 6/1992 | Rodriquez et al. | 356/39 |
| 5,155,044 | 10/1992 | Ledis et al. | 436/17 |
| 5,196,346 | 3/1993 | Lefevre et al. | 436/63 |
| 5,232,857 | 8/1993 | Lefevre et al. | 436/10 |
| 5,242,832 | 9/1993 | Sakata | 436/17 |
| 5,250,437 | 10/1993 | Toda et al. | 436/10 |
| 5,389,549 | 2/1995 | Hamaguchi et al. | 436/10 |
| 5,496,734 | 3/1996 | Sakata | 436/63 |
| 5,518,928 | 5/1996 | Cremins | 436/40 |
| 5,538,893 | 7/1996 | Sakata et al. | 436/10 |
| 5,677,183 | 10/1997 | Takarada et al. | 436/10 |
| 5,686,308 | 11/1997 | Li et al. | 436/63 |

FOREIGN PATENT DOCUMENTS 325710  8/1989  European Pat. Off. .

OTHER PUBLICATIONS

Oshiro, Iwao, et al, Clin. Biochem., 15 (1) 83–88 (1982), "New Metod for Homoglobin Determination by Using Sodium Lauryl Sulfate (SLS)".

*Primary Examiner*—Maureen M. Wallenhorst
*Attorney, Agent, or Firm*—Mitchell E. Alter

[57] ABSTRACT

A lytic reagent composition is provided which selectively stromatolyses red blood cells in a blood sample. In addition, a lytic reagent system is provided which enables the differentiation of at least three subpopulations of leukocytes. A method for using the lytic reagent system is also provided. Still further, the lytic reagent system finds use in the determination of the hemoglobin in the blood. The lytic reagent system utilizes an alkyl sulfate, polyoxyethylene based surfactant and acid with a hypertonic, alkaline, stabilizing reagent. The system and analysis method maintains the cellular morphology of the leukocytes and can be used to analyze normal and abnormal blood samples, fresh and aged blood, human and non-human animal blood samples.

24 Claims, 12 Drawing Sheets

1

REAGENT AND METHOD FOR DIFFERENTIAL DETERMINATION OF LEUKOCYTES IN BLOOD

FIELD OF THE INVENTION

The present invention relates to lytic and stabilizing reagents and a method to enable the determination of at least three populations of leukocytes in a single blood sample by means of suitable electronic instrumentation. In addition, the present invention relates to reagents and a method useful for determining total hemoglobin in blood wherein the reagents are cyanide free.

BACKGROUND OF THE INVENTION

Analysis of leukocyte populations from whole blood samples is an integral and essential part of diagnostic procedures regarding a multiplicity of pathologies. The ability to analyze the major subpopulations of leukocytes in an automated manner is essential for a rapid diagnosis of a single blood sample and for the rapid processing of many samples at once.

Traditional diagnosis of blood samples involves the smearing of a blood sample on a microscope slide, followed by manual visual analysis of the individual slide. This approach is obviously extremely time consuming as well as being subjective to the interpretation of the individual analyzing the slide. These factors have led to the development of automated leukocyte analysis utilizing flow cytometry. An essential step in the use of automated leukocyte analysis using hematology instruments is the lysis of the red blood cells. Thus far, several lysis reagents have been developed for use in whole blood samples.

U.S. Pat. No. 4,286,963 (to Ledis et al.) describes a lytic reagent and a method for achieving rapid hemolysis of erythrocytes in whole blood and automated analysis of lymphoid and myeloid subpopulations of leukocytes and the quantitative determination of hemoglobin. The lytic reagent is composed of a mixture of at least one quaternary ammonium surfactant and an aryl substituted short chain alkanol in buffered aqueous medium (pH 3.5 to 5.0). However, this reagent is limited in its ability to differentiate the leukocytes into two (2) principal subpopulations: the lymphoid and myeloid fractions.

U.S. Pat. No. 4,485,175 (to Ledis et al.) describes a reagent system and method for performing differential determinations of leukocytes into three (3) subpopulations utilizing automated cell counting equipment. This reagent system contains a blood diluent and a lytic reagent, comprising a mixture of quaternary ammonium surfactants. However, this reagent system is limited its application to effect differentiation of the leukocytes into three (3) subpopulations: lymphocytes, monocytes and granulocytes.

Quaternary ammonium surfactants are strongly hemolytic and the methods of both patents described above can cause lysis of the leukocytes. The differentiation, consequently, is based on the nuclear volumes of the leukocyte subpopulations. The application of these methods, alone or in combination with other means prohibits further refinement in the diagnostic process of various disease states based on the differences in the immunochemical response of the surface marker of the cell membrane.

U.S. Pat. No. 5,155,044 (to Ledis et al.) discloses a method and reagent system for the rapid isolation and analysis of leukocytes from a whole blood sample and enabling automated differentiation of leukocytes into five (5) subpopulations utilizing an automated hematology analyzer. The reagent system is composed of an aqueous lytic reagent which comprises formic acid (or a formic acid/acetic acid mixture), or a mixture of formic acid and saponin, and an aqueous salt quench solution. However, the saponin used in this reagent system is a natural product. As a result of being a natural product, there is the potential of their being a finite source of saponin. In addition, the quality of the saponin can vary depending on its source.

In addition, acid lysing is known in the literature and this property has been utilized in automated hematology analyzers as discussed in U.S. Pat. No. 5,155,044, U.S. Pat. No. 5,196,346, and U.S. Pat. No. 5,389,549. However, lysis of the red blood cells using acid alone takes a long time and the red cell ghosts and debris are difficult to disrupt or dissolve to a size that does not interfere with the white cell differentials when the white cell counting is accomplished using DC and RF detection techniques.

Alternative lysis reagent systems have nonionic or anionic polyoxyethylene surfactants as discussed in U.S. Pat. No. 5,116,539, U.S. Pat. No. 5,389,549 and U.S. Pat. No. 5,196,346.

U.S. Pat. No. 5,196,346 (to Leferre et al.) describes an acid based lysis system which incorporates a polyoxyethylene ether surfactant. However, this reagent system was formulated for the limited analysis of the basophil population subsequent to lysis of all other leukocytes.

U.S. Pat. No. 5,116,539 (to Hamaguchi et al.) describes a reagent system designed for the lysis of red blood cells which contains a nonionic polyoxyethylene surfactant. However, this system permits only total leukocyte counting or eosinophil counting. The differentiation and determination of other leukocyte populations cannot be done with this lysis reagent system.

U.S. Pat. No. 5,384,549 (to Hamaguchi et al.) also describes a lysis reagent system which contains a nonionic polyoxyethylene surfactant. While the lysis reagent systems presented in this patent appears to maintain the integrity of the leukocyte population better than acid lysis techniques, it is still difficult to do full analysis of the five major leukocyte subpopulations. Full analysis of leukocyte subpopulations requires differential lysis of the erythrocytes and leukocytes and three separate determinations for the identity of eosinophil, neutrophil and basophil populations in addition to the lymphocyte and monocyte populations. Additionally, this system requires a hypotonic lysing environment which is extremely shocking to the cells and makes preservation of the cells in a near native state difficult.

Previous lysis reagents utilizing polyoxyethylene based nonionic or anionic surfactants are limited in their use to either a single leukocyte cell population or when used for a multiple leukocyte subpopulation determination, the determination must be accomplished using a complex three-step flow cytometry analysis procedure. The nonionic polyoxyethylene surfactants are further limited in that they use a very hypertonic or very hypotonic environment to effectively lyse the red blood cells, which cause a traumatic osmotic shock to the cells which can be very damaging and can adversely affect the ability to analyze cells in their near native physiological state.

In addition, measuring the hemoglobin in a blood sample is another diagnostic tool when doing blood analysis. Historically, hemoglobin determinations have been performed by forming and measuring cyanide hemoglobin (Hb). However, the reagent waste from this method is of enormous environmental concern. Several cyanide-free methods for lysing erythrocytes and measuring hemoglobin (Hb) have been developed. U.S. Pat. No. 5,250,437 (to Toda et al.) and U.S. Pat. No. 5,242,832 (to Sakata) all utilize quaternary ammonium salt lysis systems for hemolyzing erythrocytes and oxidizing the hemoglobin. However, because of the harshness of the quaternary ammonium ion based systems on leukocytes, these systems cannot be used for combined leukocyte subpopulation differentiation greater than three subpopulations and hemoglobin determination, particularly if near native state leukocyte differentiation is desired.

EPO No. 0 325 710 (to Hamaguchi et al.) uses a polyethylene based nonionic surfactant for the hemolysis of red blood cells. However, the system presented by Hamaguchi et al. has limited capabilities for analysis of leukocyte subpopulations, and in a single measurement can only differentiate three subpopulations in addition to measuring the hemoglobin.

In addition, U.S. Pat. No. 4,853,338 (to Benezra et al.) also describes a method and reagent composition for determining total hemoglobin in a blood sample. The reagent composition utilizes a zwitterionic, cationic, and anionic surfactants. When the anionic surfactant is an alkyl sulfate, it is used for the determination of the hemoglobin concentration by measuring the absorbance at about 603 nm at a pH from about 11.3 to about 13.7.

In addition, Oshira et al., Clin. Biochem. 15 (1) 83–88 (1982) discuss the uses of sodium lauryl sulfate in a method for hemoglobin determination. As later explained in U.S. Pat. No. 5,242,832 (to Sakata), it is not possible with the Oshira et al. method and reagents to measure hemoglobin concentration in conjunction with differentiation of leukocyte subpopulations.

SUMMARY OF THE INVENTION

In a first embodiment, the present invention relates to a lytic reagent composition comprising a polyoxyethylene based surfactant for the determination of at least four leukocyte subpopulations in a blood sample represented by the general formula:

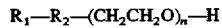

wherein $R_1$ is an alkyl, alkenyl or alkynyl group having 10 to 22 carbon atoms, $R_2$ is —O— or —COO—, and n is between 20 and 35, and an acid to adjust the pH of the lytic reagent composition to be within the range of 2.0 to 4.0.

In a second preferred embodiment, the present invention is directed to a lytic reagent composition comprising an alkali metal salt of alkyl sulfate anionic surfactant which has an alkyl chain from 10 to 18 carbon atoms; and a polyoxyethylene based surfactant for the determination of at least three leukocyte subpopulations in a blood sample represented by the general formula:

wherein $R_1$ is an alkyl, alkenyl or alkynyl group having 10 to 22 carbon atoms, $R_2$ is —O— or —COO—, and n is between 20 and 35, and an acid to adjust the pH of the lytic reagent composition to be within the range of 2.0 to 4.0.

The present invention is also related to a lytic reagent system comprising a lytic reagent defined by the first or second embodiments, and a hypertonic, alkaline stabilizing reagent composition.

Still further, the present invention is related to a method for the selective stromatolysis of red blood cells in a blood cell sample and analysis of the remaining leukocyte subpopulations comprising exposing a blood sample to the lytic reagent composition defined by the first or second embodiment for a time less than 10 seconds; adding a hypertonic alkaline stabilizing reagent composition to said exposed blood sample, wherein said stabilizing reagent composition inhibits further lytic action and stabilizes leukocytes of a hemolyzed blood sample; and differentiating leukocyte subpopulations, selected from the group consisting of lymphocytes, monocytes, basophils, neutrophils and eosinophils using an automated analyzer. When using the first embodiment, at least four subpopulations are differentiated. When using the preferred second embodiment, at least three subpopulations are differentiated.

The method of this invention also enables leukocyte differentiation of a blood sample which contains pathologically abnormal cells and blood samples wherein the source of the blood sample is a non-human animal.

The reagent and method of this invention also enable the determination of hemoglobin concentration and differentiation of subpopulations of leukocytes in a single step analysis of a single aliquot of a blood sample using the lysing reagent defined by the first or second embodiment. The mode of analysis is selected from two members of the group consisting of DC volume, RF, opacity, light scatter, fluorescence and combinations thereof.

DETAILED DESCRIPTION OF THE INVENTION

1) The Lytic Reagent Composition

Figure 1:
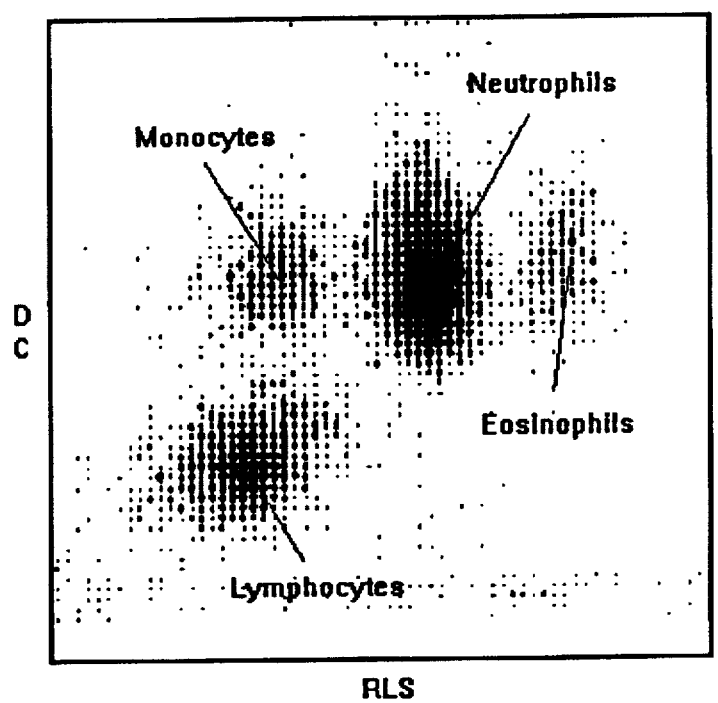
FIGS. 1–4, 7–10 and 12 are scattergrams of results obtained in accordance with the practice of the present invention as described in Examples III, VI, VII and VIII.

In the first embodiment, the present invention is directed to lytic reagent composition comprising a polyoxyethylene based surfactant and an acid to adjust the pH of the composition.

The polyoxyethylene based surfactant of the present invention has a lipophilic tail and a hydrophilic polar head group and can be represented by the formula:

wherein $R_1$ is an alkyl, alkenyl or alkynyl group having 10 to 22 carbon atoms, $R_2$ is —O— or —COO—, and n is between 20 and 35. Preferably $R_1$ is an alkyl group having 12 to 20 carbon atoms. Preferably, $R_2$ is —O—.

The polyoxyethylene based surfactant of the formula (I) can be synthesized by procedures known in the art.

It has been found that the hydrophile and the lipophile balance plays a role in the lytic potency of the nonionic polyoxyethylene based surfactant used in the lytic reagent composition of the present invention. In general, the lytic potency increases as the size of the hydrophilic polyoxyethylene head group decreases and decreases as the head group size increases.

When the polyoxyethylene units exceed 35, the reagent becomes too weak and cannot lyse the red blood cells using the preferred conditions disclosed herein. A polyoxyethylene based surfactant containing less than 20 oxyethylene units is too lytic, which causes damage to the leukocytes. This damage will prevent obtaining of four, preferably five subpopulations, of leukocytes. By having an appropriate hydrophile/lipophile balance, the polyoxyethylene based surfactant is able to selectively lyse the red blood cells without damaging the leukocytes which enables the differential measurement of at least four subpopulations of leukocytes.

The concentration of the polyoxyethylene based surfactant in the lytic reagent composition needs to be in an amount sufficient to selectively hemolyze the red blood cells in a whole blood sample, while leaving the remaining leukocytes essentially intact. The concentration of the polyoxyethylene based surfactant in the lytic reagent composition has been found to be effective in a broad range from about 5 g/L to about 120 g/L, preferably 10 g/L to 50 g/L.

The function of the acid in the lytic reagent composition is two-fold. First, it assists in red blood cell lysis by creating an acidic medium in the blood and lytic reagent mixture. Under the conditions of the present invention, the lytic reaction can take less than ten (10) seconds and preferably less than seven (7) seconds to sufficiently lyse the red blood cells and break the red cell ghosts and debris down to a level that will not interfere with the leukocyte detections and differentials. This selective and fast lytic activity preserves the leukocytes in near native conditions by avoiding prolonged exposure to the lytic reagent. For the purposes of this disclosure, near native condition means that cellular morphology is preserved so that analysis of the cellular subpopulations can be performed using histochemical or fluorescent labelling of cell surface markers.

The second function of the acid is to create only slight modifications to the leukocytes to allow appropriate separations among leukocyte subpopulations in a DC versus light scatter scattergram and a DC versus RF scattergram.

The acid is used in an amount sufficient to adjust the pH of the lytic reagent composition in the range of approximately 2.0 to 4.0. The acid will usually be an effective amount of an organic acid. Preferably, formic acid, oxalic acid, or an effective mixture of formic acid with another organic acid or an inorganic acid is used. The organic acid to be used in admixture with the formic acid can be, for example, acetic, citric, oxalic, or propionic acid or a mixture of two or more of the aforementioned acids. Inorganic acids which can be mixed with the formic acid include, but are not limited to hydrochloric and phosphoric acid.

Figure 5:
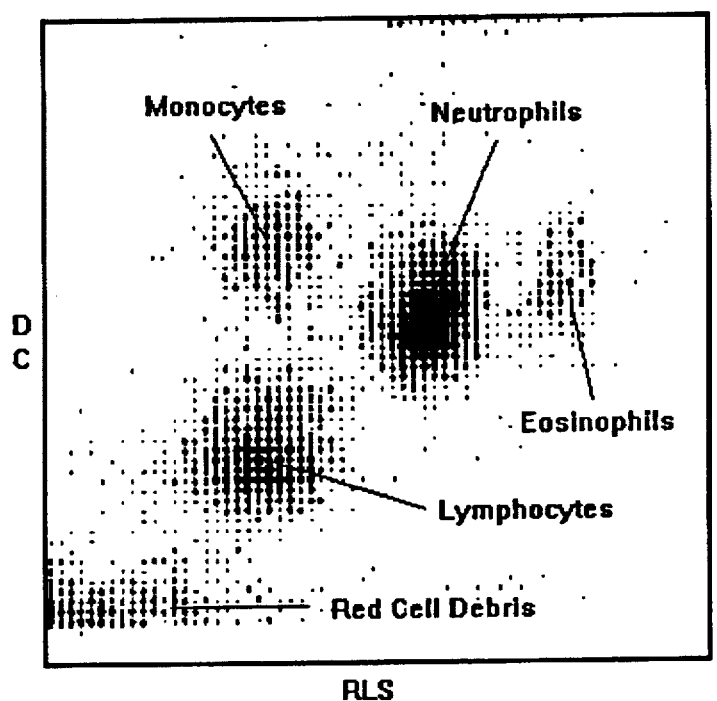
FIG. 5 is a scattergram of using a lysing reagent comprising polyoxyethylene based surfactant and an acid.

By using a polyoxethylene based surfactant with an acid (as shown in FIG. 5), it has been found that a significant amount of red blood cell debris often remains. The red cell debris can clog the flow cell and make the leukocyte differential difficult to obtain.

It has been discovered that the combination of the polyoxethylene based surfactant, acid and alkyl sulfate produces a lysing reagent that is able to selectively lyse the red blood cells and protect the leukocytes from damage. In a preferred second embodiment of the present invention, the lytic reagent composition comprises the first embodiment described above and the addition of an alkyl sulfate. The alkyl sulfate does not provide selective lysis by itself. It is believed that it is the combination of the two which enables the selective lysing of blood cells and further enables the differentiation of at least three, preferably at least four, and most preferably at least five subpopulations of leukocytes.

Figure 2:
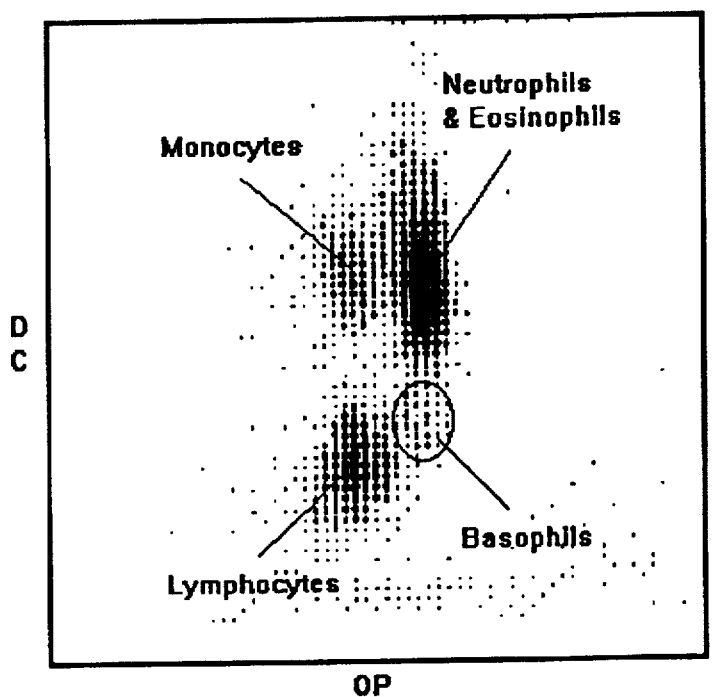
Figure 3:
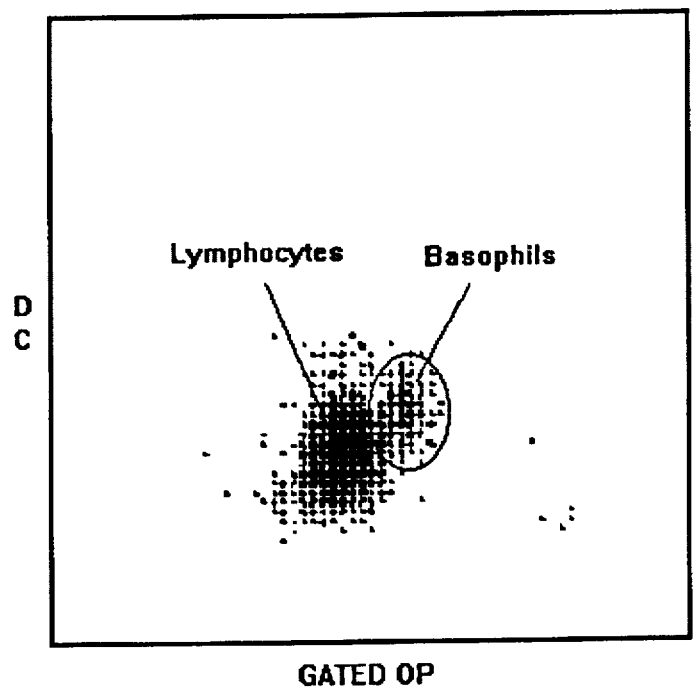

The unexpected result of the combination of the polyoxyethylene based surfactant and acid with the alkyl sulfate is clearly shown in FIGS. 1, 2 and 3 which resulted from the lytic reagent composition which contained an alkyl sulfate as compared to FIG. 5 which resulted from the lytic reagent composition which did not contain an alkyl sulfate. These figures show the elimination of the debris that is depicted in FIG. 5.

Figure 6A:
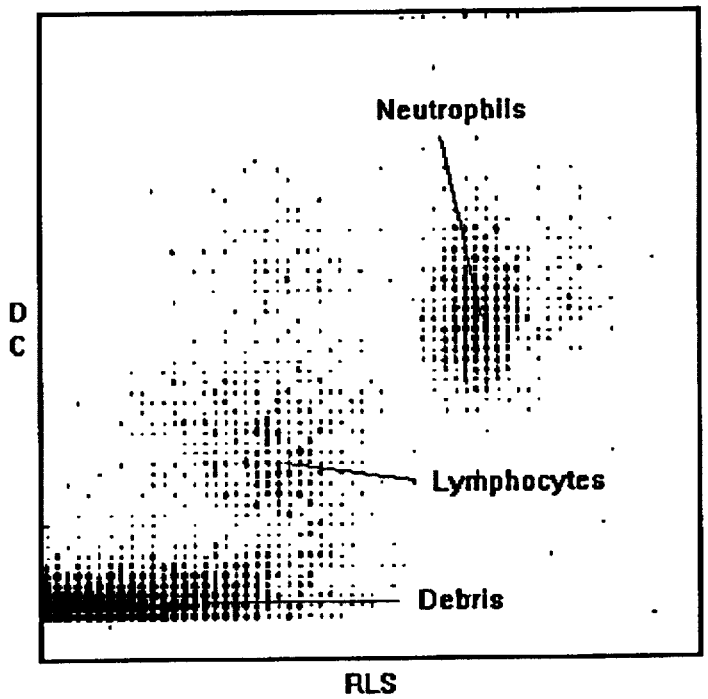
FIGS. 6A–6B are a scattergram of a lysing reagent comprising sodium dodecyl sulfate.
Figure 6B:
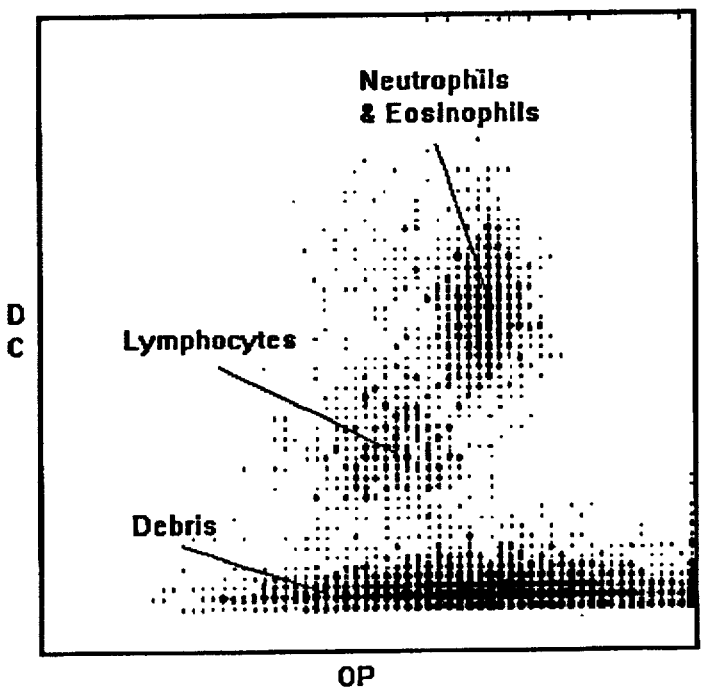
Figure 7:
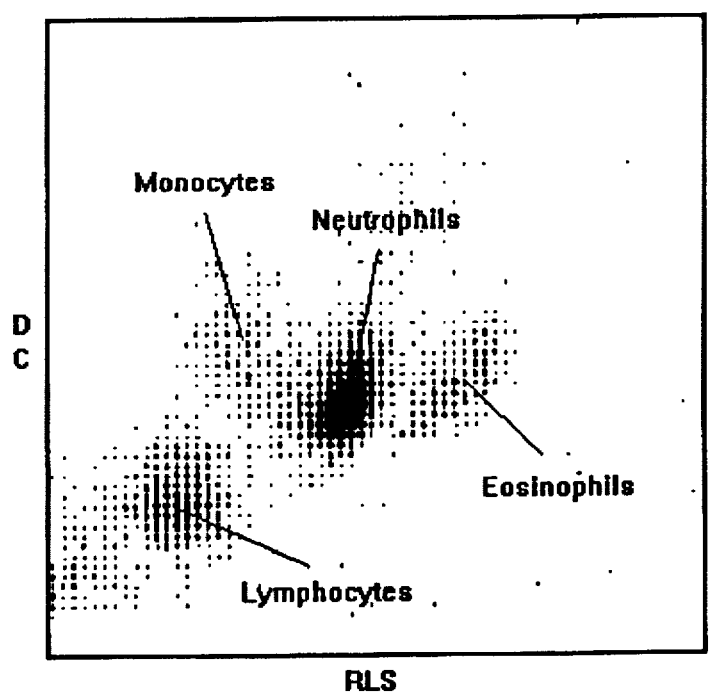
Figure 8:
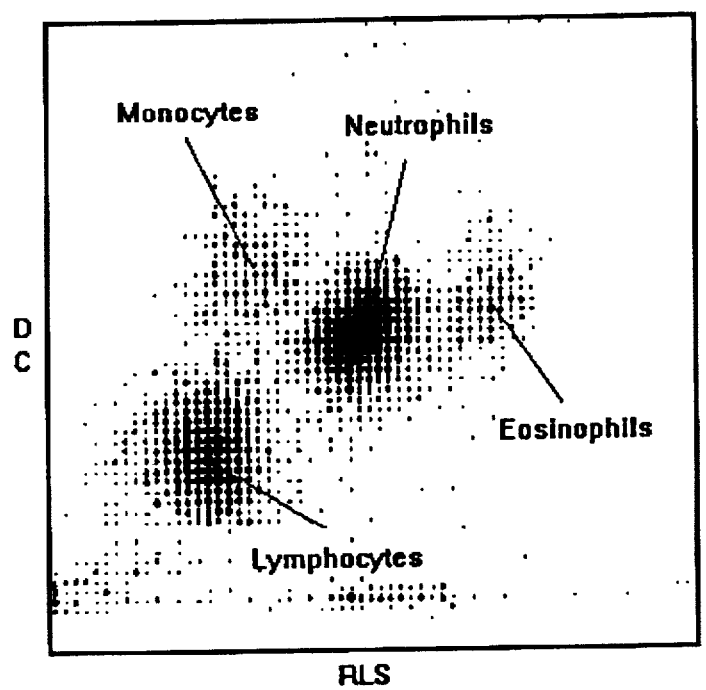

On the other hand, if the alkyl sulfate is used alone as the lysing reagent (as shown in FIGS. 6A and 6B), or an alkyl sulfate with an acid as the lysing reagent, the lysing reagent destroys the red blood cells, but leaves substantial amount of cellular debris, and also severely damages the leukocytes, especially to the monocyte subpopulation. This result occurs with a concentration of dodecyl sulfate of 0.8 g/L.

In comparison, FIGS. 1, 2 and 3 were obtained by using the same concentration of dodecyl sulfate and 20 g/L of polyoxethylene based surfactant with an acid. Therefore, it is clearly demonstrated that by using an alkyl sulfate with a polyoxethylene based surfactant and an acid results in a dramatic improvement in the selective lysing of the red blood cells.

The alkyl sulfate is an anionic surfactant such as an alkali metal salt of the $C_{10}$ to $C_{18}$ alkyl sulfates. For example, such surfactants include sodium or lithium dodecyl sulfates, or lithium or sodium tetradecyl sulfate. Preferably the surfactants are sodium dodecyl sulfate and sodium tetradecyl sulfate.

It has been found that the concentration of the alkyl sulfate is important to lyse the red blood cells. If the concentration of the alkyl sulfate is insufficient then cellular debris can make the automated differentiation of the leukocyte subpopulations difficult to obtain. If the concentration is too high, then the leukocytes will suffer damage making their differentiation at near native state extremely difficult.

The alkyl sulfate is used in an amount sufficient to lyse the red blood cells in a blood sample within less than 10 seconds. Preferably the concentration of the alkyl sulfate ranges from approximately 0.2 to 1.4 g/L, more preferably 0.4 to 1.0 g/L in the lytic reagent composition of this invention.

The mechanism by which the lytic reagent composition selectively reacts with the red and white cell fractions is not entirely clear.

Optional additives can also be included in the lytic reagent composition in concentrations that their presence is compatible with the primary functional components of the lytic reagent composition. Among these additives are preservatives which have antioxidant properties, to increase the shelf-life of the composition, and which have anti-microbial properties. Preservatives which have anti-oxidant properties include but are not limited to EDTA and butylmethylphenol. Preservatives which have anti-microbial activity include but are not limited to dimethyloldimethyl hydantoin, iodopropynylbutyl carbamate and isothiozolone derivatives.

2) The Stabilizing Reagent Composition

The present invention is also directed to a lytic reagent system comprising the lytic reagent composition and a hypertonic, alkaline stabilizing reagent.

The stabilizing reagent composition is added subsequent to red blood cell lysis to inhibit further lytic activity. More specifically, the function of the stabilizing reagent composition is to neutralize the acid in the blood mixture and prevent swelling of leukocytes so that the leukocytes are preserved for the purposes of automated analysis, including differentiation.

The stabilizing reagent composition is an aqueous buffered salt solution comprised of a simple physiological salt or salts. The salt or salts used in the stabilizing reagent composition can be a mixture of chloride salts and sulfate salts. The chloride salt can be, but is not limited to, sodium chloride or potassium chloride in a concentration of about 0.2 to 4% based on the total weight of the stabilizing reagent composition. The sulfate salt can be, but is not limited to, sodium sulfate or potassium sulfate in a concentration of about 0.3 to 8% based on the total weight of the stabilizing reagent composition. The stabilizing reagent composition is hypertonic and can have an osmolality of about 800 to 1400 mOsm. The salt concentration which affects the osmolality of the stabilizing reagent composition can vary because the volume of the stabilizing reagent composition can be adjusted relative to the lytic reagent volume so that the final osmolality of the blood sample mixture is between approximately 350 to 650 mOsm.

The buffer may be any physiological buffer including, but not limited to, potassium or sodium carbonate, potassium or sodium phosphate, Tris, HEPES, and potassium or sodium tetraborate. The pH of the stabilizing reagent composition is an approximate pH of 7 to 13, preferably having a pH of 10 to 12.5.

3) Description of Complete Lysis Reagent System for Specific RBC Lysis and Leukocyte Differentiation The present invention is also directed to a lytic reagent system comprising a lytic reagent composition to lyse red blood cells and a hypertonic, alkaline stabilizing reagent composition to be added to the blood sample subsequent to red blood cell lysis in an automated differential analysis of leukocytes.

The lytic reagent system can be used in an analysis of the treated whole blood and enables the differentiation of at least three subpopulations, preferably at least four subpopulations, and most preferably at least five subpopulations which include neutrophils, lymphocytes, monocytes, eosinophils and basophils.

The stabilizing reagent composition provides a hypertonic medium after being mixed with the blood sample mixture which contain the blood sample and lytic reagent composition so that the final osmolality of the test sample is from about 350 to 650 mOsm, preferably 450 to 550 mOsm.

For the blood sample mixture to achieve the best separation among the leukocyte subpopulations, a slight hypertonic condition is preferred, instead of a physiologically isotonic environment. The hypertonic environment created by the stabilizing reagent composition by its high physiological salt content prevents the swelling of the leukocytes that would result from their exposure to the lytic reagent composition and prevents the cell damages due to such swelling. In fact, a slight cell shrinkage occurs upon interaction with the stabilizing reagent for a few seconds, which produces a more confined cell distribution among the leukocyte subpopulations.

The generation of at least 3, preferably at least 4, and most preferably at least 5 distinct subpopulations of cells allows for the analysis of these subpopulations in a one step analysis system based on the differences in the RF, DC and light scatter profiles of the cells and circumvents the need to perform a multiple-step differential lysis of the leukocytes for full determination of the individual subpopulations, particularly the individual granulocyte subpopulations. Previous lysis reagent systems permitted at most only two parameters of DC vs. RF, or only DC analysis in a given analysis step. Thus, to fully obtain a profile of five leukocyte subpopulations, a complex method of three individual determinations using DC and RF followed by a combined analysis of the determinations was required.

Moreover, because the lytic reagent system of the present invention preserves cellular morphology, further analysis of the cellular subpopulations can be performed using histochemical and fluorescent labelling of the leukocyte cells with cell surface markers.

The leukocytes of aged and abnormal blood samples are usually fragile or sensitive to the lysing reagents and are difficult to analyze by automated blood analyzers. The harshness of most lysis reagent systems, particularly acid based lysis systems, precludes their use for analysis of any but fresh blood samples, as the cells become too fragile as they age.

The advantage of this system for preventing leukocyte damage allows this reagent system to be used not only for differential analysis of freshly collected blood samples, but also for analysis of blood samples several hours after sample collection and abnormal blood samples. The lack of harsh osmotic and acid shocks in the present invention allow for analysis of blood which is several hours old. More specifically, the present invention can be used with blood samples several hours (6 or more hours) old.

The lytic reagent system of the present invention provides an additional advantage of operating entirely at room temperatures, approximately from 18° to 28° C. Lysis reagent systems previously operated at an elevated temperature, 30° C. or higher, for adequate separation of eosinophils and basophils. This elevated temperature requirement necessitated analysis instrumentation which was significantly more complex, as the reactions must be thermostatically controlled. The present invention overcomes this need for thermostatic control by operating optimally at room temperature.

Another advantageous feature of this invention is that the lytic reagent system is less sensitive to the lipid contents of the whole blood samples, which improves the accuracy of the automated differential analysis for the high lipid blood samples, and eliminates the sample pre-dilution process which is typically required to compensate for the lipid content in the plasma.

In addition, because of the lytic reagent composition being insensitive to the lipid contents of blood samples, the lytic reagent system of this invention can be used for the differential analysis of non-human animal blood samples which can have different lipid contents. This allows a convenient method of performing leukocyte analysis of at least four subpopulations, preferably five subpopulations, in a veterinary environment.

Still further, because of the lytic reagent composition is insensitive to the lipid content, it would be expected that the lytic reagent system could be used in the differential analysis of other fluid samples which may have dramatically different lipid contents, such as bone marrow.

The lytic reagent system can be sold as a kit wherein the lytic reagent composition is packaged in a container, such as a plastic container, and the hypertonic alkaline stabilizing reagent composition is packaged in a separate container, such as a plastic container. The two containers can be packaged together in a third container, such as a box. Instructions on how to use the reagents in accordance with the present invention are preferably included inside or on or associated with the third container, or either or both of the two reagent containers.

4) Method for Stromatolysis of Red Blood Cells and Automated Differentiation and Analysis of Leukocyte Subpopulations Changes in specific subpopulations of leukocytes can be indicative of particular disease states. One of the hallmarks of the transition from HIV infection to full blown AIDS is a marked decrease in the level of lymphocytes. Fauci et al.,

*Ann. Intr. Med.*, 114, 678 (1991). Abnormal levels and morphologies of lymphocytes can also be seen with leukemias. Increased levels of both monocytes and lymphocytes are identified with acute inflammation and have been associated with diseases such as tuberculosis, granulomatous and leprosy, Gallin et al. in *Inflammation: Basic Principles and Clinical Correlations*, (1992). Many autoimmune conditions including autoimmune hemolytic anemia and lupus show increased levels of neutrophils, Malech and Gallin, *N. Engl. J. Med.*, 317, 687 (1987). Also, many parasitic infections, particularly those caused by helminth parasites, are associated with eosinophilia, Noble et al. in *Parasitology, The Biology of Animal Parasites* (1989). The present invention will be useful for the analytical and diagnostic procedures involved in identifying changes in one or more leukocyte subpopulations which may accompany any of, but not limited to, the above mentioned pathologies.

A blood sample can be obtained from a patient by conventional phlebotomy techniques. Subsequent to gathering, the blood sample is briefly mixed with the lytic reagent composition as described above.

The amount of time of exposing the blood sample to the lytic reagent composition prior to addition of the stabilizing reagent composition is important for the differentiation method for leukocyte subpopulations presented by this invention. This exposure period should preferably not exceed ten seconds, and is preferably less than seven seconds. These exposure times are specified for ambient temperature (18° to 28° C.). Increasing the temperature at which the lysis is performed correspondingly decreases the exposure time. Likewise, decreasing the temperature increases the exposure time.

After the brief exposure to the lytic reagent composition, an appropriate amount of the stabilizing reagent composition is added and the cells are analyzed within about 15 seconds after addition of the stabilizing reagent composition.

The leukocyte fraction of the whole blood sample, treated in the above procedure, can be readily differentiated into at least three subpopulations of leukocytes. Preferably at least four subpopulations and more preferably at least five subpopulations are differentiated, which include neutrophils, lymphocytes, monocytes, eosinophils and basophils.

Figure 4:
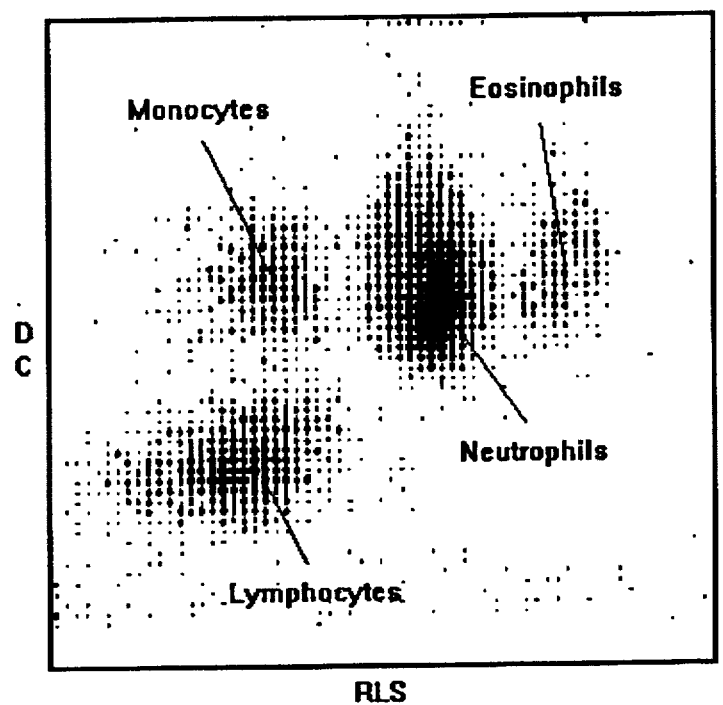
Figure 12:
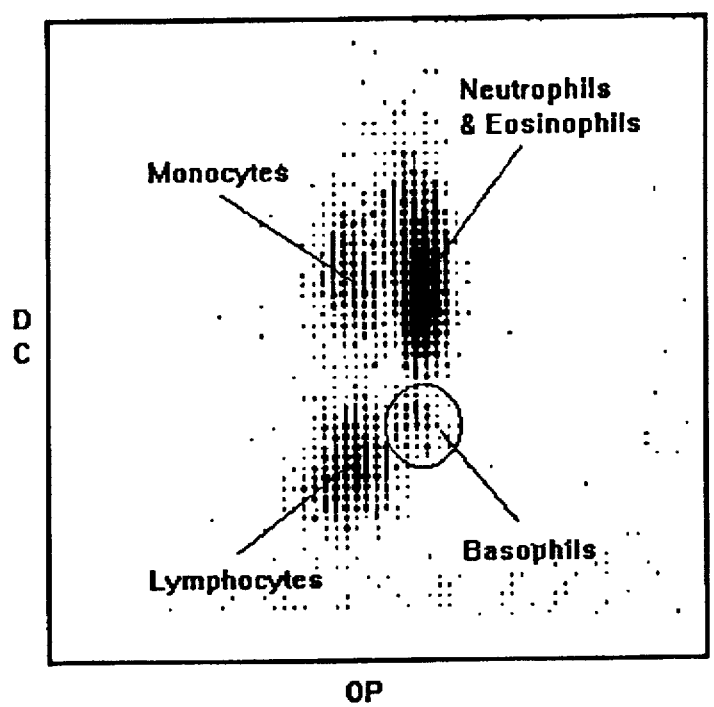

In the present invention, the first embodiment is used to obtain at least four, and preferably at least five, subpopulations of leukocytes using a one step measurement comprising DC and a member selected from the group consisting of light scatter, RF, Opacity and combinations thereof. The determination of four subpopulations using the first embodiment is shown in FIG. 4 and 12 which employs DC vs. RLS and DC vs. Coulter Opacity (function of DC and RF). Using a three dimensional analysis of LS, DC and RF enables a more accurate measurement of the basophil subpopulation to provide a total of five subpopulations of leukocytes.

The second preferred embodiment is used to obtain at least three, preferably at least four, and most preferably at least five subpopulations of leukocytes using a one step measurement comprising DC, light scatter, RF, Opacity and combinations thereof. The determination of at least three, and preferably at least four, subpopulations of leukocytes using the second preferred embodiment is shown in FIG. 1 and 2 which employs DC vs. LS and DC vs. Coulter Opacity (function of DC and RF). Using a three dimensional analysis of LS, DC and RF enables a more accurate measurement of the basophil subpopulation to provide a total of five subpopulations of leukocytes.

For the purposes of this disclosure, a single step measurement means that a single aliquot of blood can be used with the same lytic reagent composition to obtain a differentiation of the lymphocyte subpopulation with at least one other subpopulation of leukocytes consisting of eosinophils, basophils and neutrophils. Preferably, this differentiation is measured in less than 30 seconds and preferably less than 20 seconds after the addition of the lytic reagent composition.

The detection methods used for the differentiation of leukocytes by a hematology analyzer are generally described in U.S. Pat. No. 5,125,737, to Rodriguez et al., which is hereby incorporated by reference in its entirety. This reference explains differential analysis based on subpopulations' respective abilities to cause a shift in the impedance of an electric field, such a shift being proportional to the cell volume (DC); abilities to impede a radio frequency current (RF); and abilities to scatter light (LS).

Previous lysis reagent systems using polyoxyethylene based anionic or nonionic surfactants permitted only two parameter analyses in a given analysis step. Thus, to fully obtain a profile of five leukocyte subpopulations, a complex method of three individual determinations on the same sample followed by a combined analysis of the determinations was required.

Although the present method has been described in detailed terms using an analysis being conducted with combined DC, RF and LS measurements, it is within the contemplation of this invention to use the lytic reagent system in a mode of analysis selected from the group consisting of DC, RF, LS, opacity (OP), fluorescence and combinations thereof. The results of such mode of analysis can be seen from the figures wherein DC versus RF is shown in FIG. 2; and DC versus LS is shown in FIG. 1.

5) Method for Hemoglobin Determination

More than 300 abnormal hemoglobins have been discovered upon examination of patients with clinical symptoms and by electrophoretic surveys of a clinically normal population. Many of these abnormalities result in clinical pathologies having altered hemoglobin levels or hemoglobin having an altered ability to bind oxygen. Among these diseases are sickle cell anemia, both $\alpha$- and $\beta$-thalassemias and hemoglobin M, Stamatoyannopoulos G. et al. (Eds), *Molecular Basis of Blood Disorders* (1986).

An ability to measure hemoglobin in blood samples is an essential part of diagnostic analysis and is also important for monitoring responsiveness to therapies directed towards diseases which affect hemoglobin and to therapies which are directed towards other diseases but which may have adverse side effects on the hemoglobin level. Ideally, one would like to be able to accomplish multiple diagnostic analyses in a single automated step.

The present invention allows for the analysis of at least three, preferably four, and more preferably five subpopulations of leukocytes in conjunction with a determination of the hemoglobin.

Lysis of erythrocytes with the lytic reagent composition causes the release of hemoglobin. Addition of the stabilizing reagent composition results in the formation of a stable chromogen which has a maximum absorbance peak at approximately 540 nm and a shoulder at 570 nm.

This system provides several advantages over the methods of hemoglobin measurement of the prior art. Unlike the previous methods, the present invention allows for the differentiation and analysis of leukocyte subpopulations in their near native state along with a determination of the hemoglobin concentration. The stabilizing reagent composition converts the hemoglobin to the chromogen in less than 10 seconds, allowing for rapid automated analysis. The chromogen once formed is stable for up to approximately 30 minutes.

EXAMPLE I

Lytic Reagent Composition a) A lytic reagent composition encompassing the polyoxyethylene based surfactant of structure I has been formulated with the following composition:

A polyoxyethylene based surfactant with formula:

$$C_{18}H_{37}O(CH_2CH_2O)_nH$$

where n is 30, was dissolved in deionized water at a concentration of 20 g/L. 0.8 g/L of sodium dodecylsulfate (SDS, Aldrich) was added. Formic acid was used to adjust the pH to 2.8. In addition, the following preservatives were added: 0.3 g/L EDTA, 0.5 g/L Proclin 300 (Rohm & Haas Co.), and 0.05 g/L 2,6-Ditert-butyl-4-methylphenol (predissolved in ethanol);

b) A lytic reagent composition encompassing the polyoxyethylene based surfactant of structure I has been formulated with the following composition:

A polyoxyethylene based surfactant with formula:

$$C_{16}H_{35}O(CH_2CH_2O)_nH$$

where n is 25, was dissolved in deionized water at a concentration of 20 g/L. 0.8 g/L of sodium dodecylsulfate was added. 1.2 mL/L formic acid was used to adjust the pH to 2.8;

c) A lytic reagent composition encompassing the polyoxyethylene based surfactant of structure I has been formulated with the following composition:

A polyoxyethylene based surfactant compound with formula:

$$C_{18}H_{37}O(CH_2CH_2O)_nH$$

where n is 30, was dissolved in deionized water at a concentration of 20 g/L. 0.8 g/L of sodium dodecylsulfate was added. A 1:1 ratio of formic acid/phosphoric acid mixture was used to adjust the pH of the composition to 2.5. In addition, the following preservatives were added: 0.3 g/L EDTA, 0.2 g/L Proclin 300, and 0.05 g/L 2,6-Di-tert-butyl-4-methylphenol (predissolved in ethanol).

d) A lytic reagent composition encompassing the polyoxyethylene based surfactant of structure I has been formulated with the following composition:

A polyoxyethylene based surfactant compound with formula:

$$C_{18}H_{37}O(CH_2CH_2O)_nH$$

where n is 30, was dissolved in deionized water at a concentration of 20 g/L. 2.1 g/L of Polystep B-25 (38%) from Stepan was added. Polystep B-25 is a brand name for a sodium decyl sulfate product. 1.2 mL/L formic acid was used to adjust the pH to 2.8; In addition, the following preservatives were added: 0.3 g/L EDTA, 0.2 g/L Proclin 300, and 0.05 g/L 2,6-Di-tert-butyl-4-methylphenol (predissolved in ethanol).

e) A lytic reagent composition encompassing the polyoxyethylene based surfactant of structure I has been formulated with the following composition:

A polyoxyethylene based surfactant compound with formula:

$$C_{18}H_{37}O(CH_2CH_2O)_nH$$

where n is 30, was dissolved in deionized water at a concentration of 20 g/L. 0.9 g/L of Lanette E (90%) from Henkel Canada Ltd. was added. Lanette E is a brand name for a sodium cetearyl sulfate product. Formic acid was used to adjust the pH to 2.8.

EXAMPLE II

Stabilizing Reagent Composition a) Carbonate Buffer Based Stabilizing Reagent A stabilizing reagent has been prepared by dissolving 14.5 g/L of NaCl, 31.0 g/L of $Na_2SO_4$ and 7.0 g/L of $Na_2CO_3$ buffer in deionized water. The pH was adjusted to 12.0 by 50% NaOH aqueous solution. The osmolality of this reagent was about 1160 mOsm.

b) Phosphate Buffer Based Stabilizing Reagent

A stabilizing reagent has been formulated as described above and contains 6.4 g/L $Na_2HPO_4$, 9.6 g/L $Na_3PO_4$, 14.5 g/L NaCl and 31.0 g/L $Na_2SO_4$, pH adjusted to 12. The osmolality of this reagent was about 1173 mOsm.

EXAMPLE III

Lysis of RBC and Differentiation of Human Leukocyte Populations in a whole blood sample The lytic reagent system of this invention was prepared in deionized water from reagent grade chemicals and polyoxyethylene based surfactant compounds of industrial purity.

a) 20 g of the polyoxyethylene based surfactant described in Example I a) and 0.8 g of sodium dodecylsulfate were dissolved in 1 L of water. The pH of the surfactant solution was adjusted to 2.8 by formic acid. 0.3 g of EDTA and 0.5 g of Proclin 300 were added as antioxidant and antimicrobial preservatives, respectively. To 34 ml of a whole blood sample, 618 ml of the lytic reagent composition was added and the mixture was gently mixed by swirling for 5 seconds at room temperature (approximately 21° C.).

The lysing reaction was retarded by the addition 323 ml of an stabilizing reagent composition containing 14.5 g/L of NaCl, 31 g/L of $Na_2SO_4$ and 7.0 g/L of $Na_2CO_3$, pH 12.0. The blood mixture was gently mixed and ready for differential analysis 13 seconds after the addition of the stabilizing reagent. The final blood mixture was kept at neutral pH (about 7) and in hypertonic condition with a osmolality about 506 mOsm. Three-dimensional differential analysis was conducted on a COULTER® STKS hematology analyzer with DC, RF and light scatter measurements utilizing a focus flow technique and ISOTON® III diluent as a sheath fluid. The resulting scattergrams are illustrated in FIG. 1 and FIG. 2. Four distinct subpopulations of leukocytes were identified and quantified in the DC vs. rotated light scatter (RLS) scattergram, FIG. 1. FIG. 2 illustrates the separated leukocyte subpopulations in the scattergram of DC vs. Opacity (a function of RF and DC). A fifth subpopulation of the leukocyte, basophils, is isolated by gating out other overlapping subpopulations in the DC vs. opacity scattergram. The isolated basophil population is depicted in the scattergram illustrated in FIG. 3.

b) Using the procedure describe above with the lytic reagent composition of Example I b), selective lysis of the red blood cells and differential analysis of leukocytes subpopulations was performed. FIG. 4 and 12 show four leukocyte subpopulations seen with the DC vs. light scatter and DC vs. Opacity scattergrams obtained from this analysis. A fifth leukocyte subpopulation, basophils, can be obtained by gating the acquired data as described above.

c) Using the procedure described above with the lytic reagent composition of Example I c), selective lysis of the red blood cells and differential analysis of leukocytes subpopulations was performed. The obtained DC vs. light scatter scattergram has four distinctly separated leukocyte subpopulations including lymphocytes, monocytes, neutrophils and eosinophils. The basophils can be obtained by gating the acquired data as described above.

EXAMPLE IV

RBC Lysis and Leukocyte Differentiation Using Lytic Reagent Composition Without Alkyl Sulfate A lytic reagent was prepared as described above with a composition of Example I a) except that SDS was not added. The procedure of Example III was repeated utilizing this lytic reagent and the stabilizing reagents described in Example III for leukocyte differentials of whole blood samples. FIG. 5 shows the obtained DC vs. light scatter scattergram. Although a similar leukocyte subpopulation separation was obtained in the absence of SDS, a significant amount of undissolved red blood debris were counted during the differential measurement, as shown at the bottom of the scattergram. These undissolved debris causes frequent flow cell clogging and affect the white cell counting.

EXAMPLE V

RBC Lysis and Leukocyte Differentiation of A Lytic Reagent Composition Containing Alkyl Sulfate Only A lytic solution containing 0.8 g/L SDS only was prepared. The composition did not include either the polyoxyethylene based surfactant nor acid. The procedure of Example III was repeated using this solution as the lytic reagent and the stabilizing reagent described in Example III for leukocyte differentiations of whole blood samples.

FIGS. 6A and 6B show the obtained DC vs. RLS and DC vs. OP scattergrams. As shown, there is a significant leukocyte cell damage occurring, especially the monocyte subpopulation which is almost completely destroyed. In addition, large quantities of debris is counted during the measurement. This debris could include the damaged leukocytes and undissolved red cell debris.

EXAMPLE VI

RBC Lysis and Differentiation of Non-Human Animal Leukocyte Populations

Several veterinary whole blood samples were analyzed using the same lytic reagent composition and stabilizing reagent composition and the method described in Example III, except that the lytic reaction time varied among the different species from 2 to 7 seconds and the stabilizing reagent composition interaction time was from 6 to 20 seconds. The lytic reaction times and stabilizing reagent interaction times are consistent between different experiments performed on a given species. FIGS. 5 and 6 show the resulting DC vs. light scatter scattergrams of a canine whole blood sample and a simian whole blood sample, respectively.

As shown by the scattergrams, although each species has its own characteristics in terms of the respective subpopulation distribution, the leukocyte subpopulations including lymphocytes, monocytes, neutrophils and eosinophils within a species, are clearly distinct from each other. Among different species, the lytic reaction time and reagent volume can be varied in order to obtain the best differential results, but such variations can be easily accomplished by automated blood analyzers.

This invention allows an ability to differentiate at least four different subpopulations of leukocytes, i.e., lymphocytes, monocytes, neutrophils and eosinophils, with veterinary whole blood samples utilizing an automated method.

EXAMPLE VII

Figure 9A:
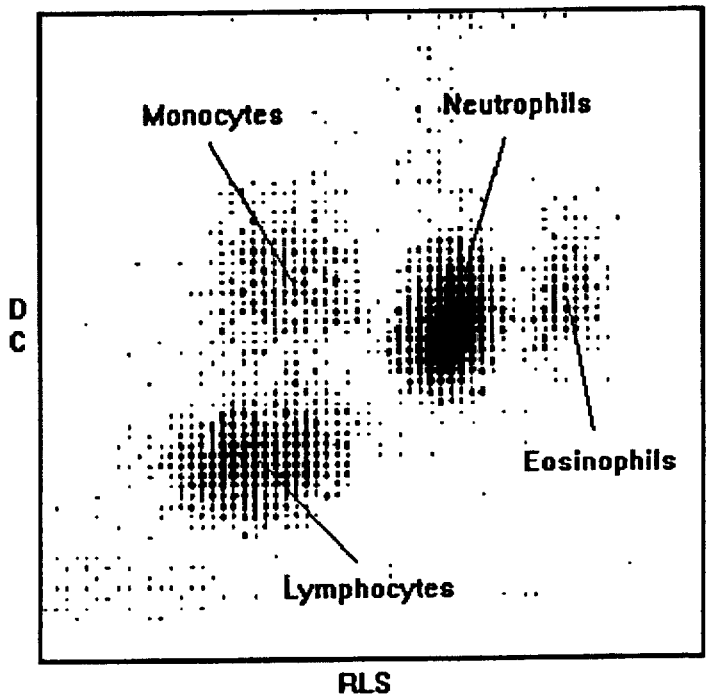
Figure 9B:
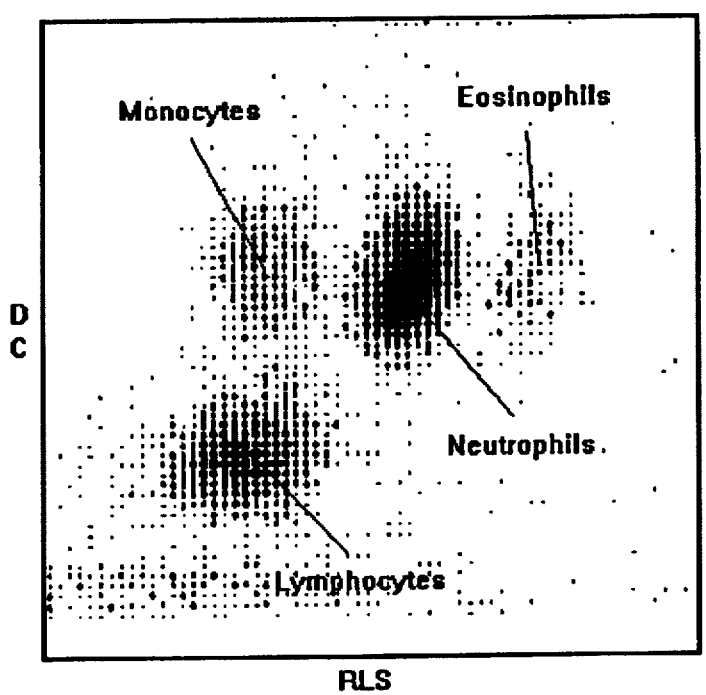

Lysis RBC and Differentiation of Human Leukocyte Populations From Aged Blood Samples The procedure of Example III was repeated utilizing the same lytic and stabilizing reagents for leukocyte differentials of a whole blood sample several hours after gathering for direct comparison of the differentiation with fresh blood samples. The sample was stored at room temperature, approximately 21° C. As clearly shown in FIG. 9, similar leukocyte subpopulation profiles were obtained for a fresh blood (10 minutes after collection), FIG. 9A, and the blood sample that was 16 hours old, FIG. 9B, demonstrating that this invention can be used for leukocyte differentiation and analysis several hours after blood sample collection.

EXAMPLE VIII

Lysis RBC and Differentiation of Abnormal Human Leukocyte Populations

Figure 10:
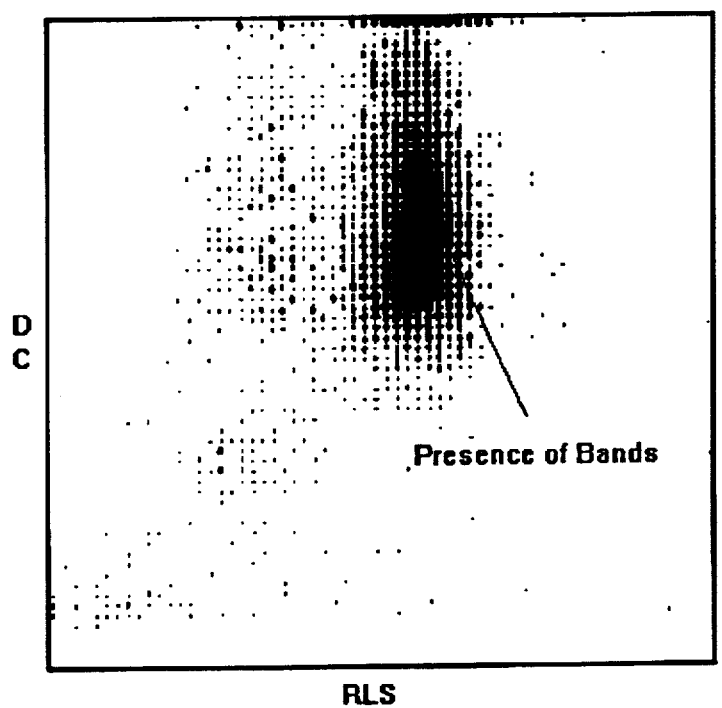

The procedure of Example III was repeated for leukocyte differentiation of blood sample from a 21 years old liver transplant patient after the surgery. As seen in FIG. 10, analysis of the blood sample using the lytic reagent system and automated hematology analysis showed the presence of immature granulocytes, and indicated the pathology by an extreme abnormal leukocyte differentials.

EXAMPLE IX

Hemoglobin Determination of Whole Blood Samples

Figure 11:
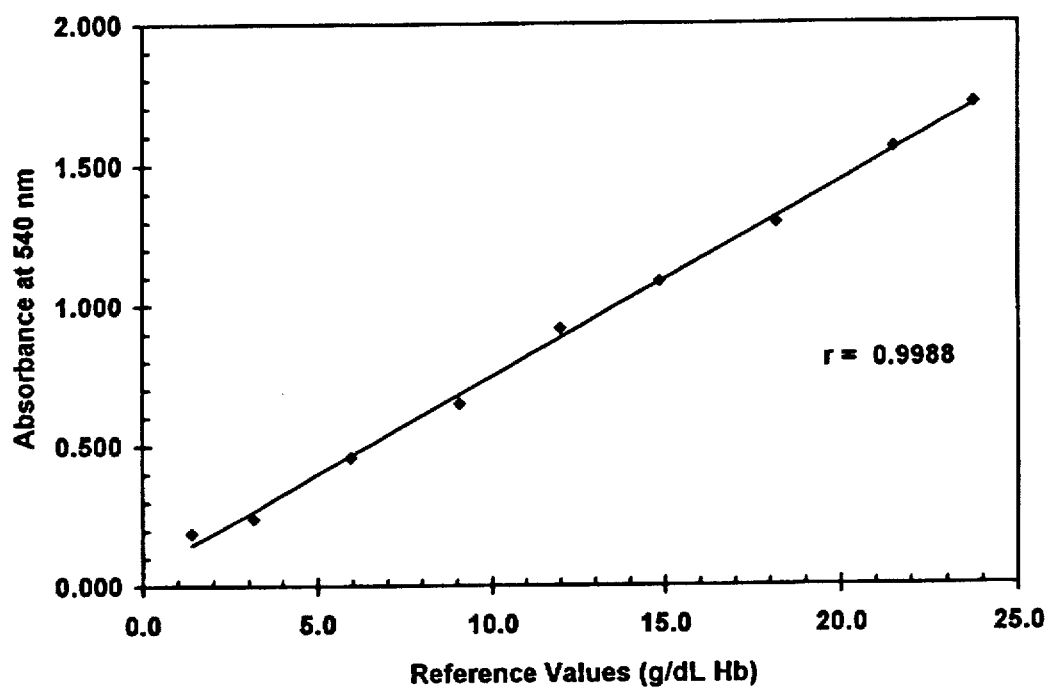
FIG. 11 is a graph of hemoglobin correlation curve between the absorbance of the chromogen and the reference value of the hemoglobin concentration.

The lytic reagent system of Example III was used in the determination of hemoglobin in whole blood samples. 10 µl of whole blood were mixed with 540 µl of the lytic reagent composition and gently mixed for 4 seconds. 208 µl of the stabilizing reagent composition was added and after 15 seconds, an absorption profile of the resulting chromogen was measured on a Beckman DU 7500 spectrophotometer. The chromogen has a maximum absorption peak at 540 nm with a shoulder at 570 nm. The chromogen formed in less than 10 seconds after addition of the stabilizing reagent and was stable for more than 30 minutes. A series of hemoglobin reference samples were analyzed by the procedure described above. The reference samples were prepared by suspending a known amount of washed red blood cells in a biological buffer medium, and their hemoglobin concentrations were determined by using the standard Drabkin's reagent and method. These samples are stable for three months under refrigeration. The absorbances obtained from these samples were plotted against their hemoglobin concentration determined by Drabkin's method. The resulting correlation curve is shown in FIG. 11. The linear response of the absorbance to the hemoglobin concentration, with a correlation coefficient of 0.999, clearly demonstrates the feasibility of using the lytic reagent system of this invention for automated hemoglobin analysis, in conjunction with the leukocytes differentiation.

EXAMPLE X

Whole Blood Leukocyte Differentials by Fluorescence

The lytic reagent system of Example III has been used in conjunction with fluorescent labeling of cell surface markers. A blood sample is stained with an aqueous dye solution at a 10:1 ratio for a few minutes. 28 mL of the stained blood sample is aspirated to a hematology analyzer with the same reagent volumes and reaction times to the regular 5-part differential analysis described in Example III. The sample mixture is analyzed by fluorescence and DC. The major populations, i.e., lymphocytes, monocytes, neutrophils and eosinophils, can be clearly separated. This not only demonstrates the preservation of cell surface morphology with the lytic reagent system, but also allows for further diagnostic capabilities based on alterations of cell surface markers on any one of the five subpopulations of leukocytes which can be differentially identified.

What is claimed is:

1. A lytic reagent composition comprising:
   a. an alkali metal salt of alkyl sulfate anionic surfactant which has an alkyl chain from 10 to 18 carbon atoms in a concentration from about 0.4 g/L to about 1.0 g/L;
   b. a polyoxyethylene based surfactant for the determination of at least three leukocyte subpopulations in a blood sample represented by the general formula:

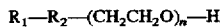

wherein $R_1$ is an alkyl, alkenyl or alkynyl group having 10 to 22 carbon atoms, $R_2$ is —O— or —COO—, and n is between 20 and 35; and
   c. acid to adjust the pH of the lytic reagent composition to be within the range of 2.0 to 4.0 wherein the acid comprises an effective mixture of formic acid and an acid selected from the group consisting of acetic, citric, oxalic, propionic, hydrochloric and phosphoric and mixtures thereof.

2. The lytic reagent composition of claim 1, wherein $R_1$ is an alkyl group having 12 to 20 carbon atoms.

3. The lytic reagent composition of claim 2, wherein said polyoxyethylene based surfactant in the lytic reagent composition is at a concentration of 5 g/L to 120 g/L.

4. A kit for determination of subpopulations of leukocytes comprising:
   a. the lytic reagent composition of claim 1, and
   b. a hypertonic, alkaline stabilizing reagent composition.

5. The kit of claim 4, wherein the alkaline stabilizing reagent composition comprises chloride salts, sulfate salts and a buffer.

6. The kit of claim 5, wherein the alkaline stabilizing reagent composition further comprises a buffer to adjust the pH of said stabilizing reagent composition to a pH of 7 to 13.

7. A lytic reagent system, comprising:
   a. a lytic reagent composition comprising an alkali metal salt of alkyl sulfate anionic surfactant which has an alkyl chain from 10 to 18 carbon atoms in a concentration from about 0.4 g/L to about 1.0 g/L; a polyoxyethylene based surfactant for the determination of at least three leukocyte subpopulations in a blood sample represented by the general formula:

wherein $R_1$ is an alkyl, alkenyl or alkynyl group having 10 to 22 carbon atoms, $R_2$ is —O— or —COO—, and n is between 20 and 35; and an acid to adjust the pH of the lytic reagent composition to be within the range of 2.0 to 4.0, and
   b. a hypertonic, alkaline stabilizing reagent composition.

8. The lytic reagent system of claim 7, wherein the hypertonic alkaline stabilizing reagent composition comprises chloride salts, sulfate salts and a buffer.

9. The lytic reagent system of claim 8, wherein the hypertonic alkaline stabilizing reagent composition comprises:
   a. a chloride salt selected from the group consisting of sodium chloride and potassium chloride in an amount of 0.2% to 4% by weight based on the total weight of the stabilizing reagent composition; and
   b. a sulfate salt selected from the group consisting of sodium sulfate and potassium sulfate in an amount of 0.3% to 8% by weight based on the total weight of the stabilizing reagent composition.

10. The lytic reagent system of claim 9, which further comprises a buffer to adjust the pH of said stabilizing reagent composition to a pH of 7 to 13.

11. A method for the selective stromatotysis of red blood cells in a blood cell sample and differentiation of the remaining leukocyte subpopulations comprising:
   a. exposing a blood sample to a lytic reagent composition comprising a polyoxyethylene based surfactant for the determination of at least four leukocyte subpopulations in a blood sample represented by the general formula:

wherein $R_1$ is an alkyl, alkenyl or alkynyl group having 10 to 22 carbon atoms, $R_2$ is —O— or —COO—, and n is between 20 and 35; and acid to adjust the pH of the lytic reagent composition to be within the range of 20 to 4.0 for a time less than 10 seconds;
   b. adding a hypertonic alkaline stabilizing reagent composition to said exposed blood sample to form a hypertonic medium, wherein said stabilizing reagent composition inhibits further lytic action and stabilizes leukocytes of said blood sample; and
   c. differentiating at least four leukocyte subpopulations, selected from the group consisting of lymphocytes, monocytes, basophils, neutrophils and eosinophils in a single step measurement using an automated analyzer.

12. The method of claim 11 wherein the stabilizing reagent composition stabilizes the leukocyte subpopulations at a neutral pH and in a hypertonic medium of osmolality from 350 to 650 mOsm.

13. The method of claim 11 which further comprises determining hemoglobin concentration in said exposed blood sample photometrically at a predetermined wavelength.

14. A method for differentiation of at least four subpopulations of leukocytes in a blood sample comprising:
   a. analyzing a blood sample which has been subjected to the method of claim 11 in a single step measurement by an instrument, wherein said single step measurement is performed with a single aliquot of said blood sample to obtain at least four subpopulations of leukocytes, said analysis selected from two methods of the group consisting of:
      (1) DC volume,
      (2) RF,
      (3) opacity,
      (4) light scatter, and
      (5) fluorescence; and
   b. reporting the results of such analysis in an instrument.

15. The method of claim 14 wherein one of the methods of analysis is DC volume.

16. The method of claim 14 wherein one of the at least four subpopulations of leukocytes is basophils.

17. The method of claim 14 wherein one of the at least four subpopulations of leukocytes is eosinophils.

18. A method for the selective stromatolysis of red blood cells in a blood cell sample and differentiation of the remaining leukocyte subpopulations comprising:
   a. exposing a blood sample to the lytic reagent composition of claim 7 for a time sufficient to lyse red blood cells;
   b. adding a hypertonic alkaline stabilizing reagent composition to said exposed blood sample, wherein said stabilizing reagent composition inhibits further lytic action and stabilizes leukocytes of said blood sample; and
   c. differentiating at least four leukocyte subpopulations, selected from the group consisting of lymphocytes, monocytes, basophils, neutrophils and eosinophils using an automated analyzer.

19. The method of claim 18 wherein the differentiating of at least four leukocyte subpopulations is performed in a single step measurement.

20. The method of claim 19 wherein at least five leukocyte subpopulations are differentiated.

21. The method of claim 18 which further comprises the determination of hemoglobin concentration in said exposed blood sample photometrically at a predetermined wavelength.

22. The method of claims 11 or 18, wherein said blood sample contains a pathologically abnormal population of cells.

23. The method of claims 11 or 18, wherein the source of the blood sample is a non-human animal.

24. A method for differentiation of at least four subpopulations of leukocytes in a blood sample comprising:
   a. analyzing a blood sample which has been subjected to the method of claim 18 in a single step measurement by an instrument, wherein said single step measurement is performed with a single aliquot of said blood sample to obtain at least four subpopulations of leukocytes, said analysis selected from two methods of the group consisting of:
      (1) DC volume,
      (2) RF,
      (3) opacity,
      (4) light scatter, and
      (5) fluorescence; and
   b. reporting the results of such analysis in an instrument.

* * * * *